(12) United States Patent
Bates et al.

(10) Patent No.: US 7,226,766 B2
(45) Date of Patent: Jun. 5, 2007

(54) S-METHYLCYSTEINE, S-ETHYLCYSTEINE, AND RELATED S-ALKYLTHIOLS AS ANTAGONISTS TO THE EFFECTS OF S-NITROSOTHIOLS AND NITRIC OXIDE

(75) Inventors: James N. Bates, Iowa City, IA (US); Stephen J. Lewis, Athens, GA (US)

(73) Assignee: University of Iowa Research Foundation, Iowa City, IA (US)

( * ) Notice: Subject to any disclaimer, the term of this patent is extended or adjusted under 35 U.S.C. 154(b) by 452 days.

(21) Appl. No.: 09/879,710

(22) Filed: Jun. 12, 2001

(65) Prior Publication Data

US 2002/0187137 A1    Dec. 12, 2002

(51) Int. Cl.
*C12N 9/00* (2006.01)
(52) U.S. Cl. ..................................... 435/183
(58) Field of Classification Search ................ 514/921, 514/706; 424/70.51; 554/101
See application file for complete search history.

(56) References Cited

U.S. PATENT DOCUMENTS

| 3,892,852 | A | * | 7/1975 | Joullie et al. | |
| 4,772,591 | A | * | 9/1988 | Meisner | 514/62 |
| 5,552,267 | A | | 9/1996 | Stern | 435/1.1 |
| 5,596,011 | A | | 1/1997 | Repine | 514/369 |
| 5,762,922 | A | | 6/1998 | Noble | 424/85.4 |
| 5,780,489 | A | | 7/1998 | Brooks | 514/369 |
| 5,827,886 | A | | 10/1998 | Hersh | 514/562 |
| 5,906,811 | A | | 5/1999 | Hersh | 424/54 |
| 5,972,993 | A | | 10/1999 | Ptchelintsev | 514/449 |
| 6,057,367 | A | | 5/2000 | Stamler | 514/561 |

OTHER PUBLICATIONS

Chemical Abstracts Registry file Printout of S-Methyl cysteine, 2002.*
Chemical Abstracts Registry Printout of S-Methyl Cysteine, 2002.*
Volker Burkart et al.; Suppression of nitric oxide toxicity in islet cells by a-tocopherol; 0014-5793/95/59.50 C 1995 Federation of European Biochemical Societies; Germany Federation of European Biochemical Societies: Apr. 6, 1995: pp. 259-263.
Souichi Satoh et al.; NO Donors Stimulate Noradrenaline Release From Rat Hippocampus in a Calmodulin-Dependent Manner in the Presnece of L-Cysteine; Journal of Cellular Physiology 169:87-96 (1996): 1996 Willey-Liss, Inc.: Japan.
Mary Ann De Groote et al.; Homocysteine Antagonism of Nitric Oxide-Related Cytostasis in Salmonella typhimurium; Science, Apr. 19, 1996; vol. 272; USA.
Zhihui Zhao et al.; Reduced glutathione prevents nitric oxide-induced apoptosis in vascular smooth muscle cells; Biochimica et Biophysica Acts (BBA);1997; pp. 143-152; 0167-4889/97/$17.00 C 1997 Elsevier Science B.V. All rights reserved. PII S0167-4889(97)00093-1; Elsevier; USA.
Neil Hogg, et al.; S-Nitrosoglutathione as a substrate for y-glutamyl transpeptidase; 1997; pp. 477-481; Biochem, J. (1997) 323; Great Britain.

* cited by examiner

*Primary Examiner*—Michael Meller
(74) *Attorney, Agent, or Firm*—McKee, Voorhees & Sease, P.L.C.

(57) ABSTRACT

A method of inhibiting the actions of S-nitrosothiols and nitric oxide which often occur in conditions such as septic shock, chronic or acute pain syndromes, uterine hypotonus, or certain gastrointestinal disorders. The method involving inhibiting the cellular binding of S-nitrosothiols to their cellular receptors or the signal transduction that would result. This is accomplished by administering an S-alkylthiol such as S-methyl-L-cysteine or S-ethyl-L-cysteine to a patient as an antagonist of S-nitrosothiol.

8 Claims, 6 Drawing Sheets

S-METHYLCYSTEINE, S-ETHYLCYSTEINE, AND RELATED S-ALKYLTHIOLS AS ANTAGONISTS TO THE EFFECTS OF S-NITROSOTHIOLS AND NITRIC OXIDE

FIELD OF THE INVENTION

This invention is directed to therapeutic methods involving administration of antagonists of S-nitrosothiols. S-nitrosothiols are naturally occurring compounds related to nitric oxide which are involved in the regulation of blood pressure, pain perception, control of smooth muscle tone, and numerous other functions in humans.

BACKGROUND OF THE INVENTION

Nitric oxide is a major intercellular signal in humans and other animals that affects many different organ systems. Important actions caused by nitric oxide include vasodilation, smooth muscle relaxation in the gastrointestinal tract, lungs, and uterus, and many neurological functions including pain perception. Many of the actions of nitric oxide are actually caused by compounds, known as S-nitrosothiols or thionitrites, that are derived from nitric oxide and specific thiols. Some of the actions of S-nitrosothiols occur at stereospecific recognition sites that are selective for specific nitrosothiols.

One pathological condition in humans that is caused by the overproduction of nitric oxide is septic shock. The profound hypotension, tissue ischemia, and organ failure of septic shock are rare sequellae to infection yet septic shock is the leading cause of death in intensive care units. The hypotension is largely the result of massive vasodilation in the patient with hypoperfusion and organ failure, including cardiac failure, exacerbating the problem. Vasodilation is initiated by bacterial endotoxins which trigger a series of host defense mechanisms including greatly increased expression of the inducible isozyme of nitric oxide synthase (iNOS). Treatment of septic shock, in addition to treatment of the underlying infection, consists of administration of intravenous fluids and vasopressors, although these therapies are less effective in septic patients than non-septic patients. Decreasing the production of nitric oxide (NO) with inhibitors of nitric oxide synthase such as $N\omega$-nitro-L-arginine methyl ester (L-NAME) or L-$N^G$methylarginine (L-NMMA) is a logical therapy, but results in both animals and humans have not been encouraging. Heart failure and continued high mortality commonly follow such treatment.

Current treatment options for hypotension or shock from such conditions such as septic shock, toxic shock syndrome, spinal cord injury, effects of anesthetics, and anaphylaxis, etc. are limited to vasoconstricting agents that have many deleterious side effects that limit their effective therapeutic usage.

It therefore can be seen that there is a continuing need for the development of effective pharmacological treatments to counteract hypotension and shock. In particular, there is no effective treatment presently available that specifically counteracts the hypotension caused by the relative overproduction of nitric oxide and nitrosothiols as present in such conditions as septic shock. This invention has as its primary objective the fulfillment of this need.

Other objectives of the present invention include both processes, compositions and treatments useful to treat the undesired effects of nitric oxide and nitrosothiol production. Conditions other than hypotension that might benefit from inhibition of the actions of nitric oxide and nitrosothiols includes but are not limited to, chronic and acute pain, hypoxemia secondary in part to the loss of hypoxic pulmonary vasoconstriction, uterine atony, and decreased tone and peristalsis of gastrointestinal smooth muscle.

SUMMARY OF THE INVENTION

The inventors have discovered that the use of certain S-alkylthiols, including but not limited to S-ethylcysteine, S-methylcysteine, S-methylcysteamine, S-ethylcysteamine, S-ethylglutathione, S-methylglutathione, S-methylglutathione, S-methylcoenzyme A, and S-ethylcoenzyme A in treatment effective amounts as antagonists to S-nitrosothiols will significantly reduce risk of hypotension, tissue ischemia, central nervous system injury, or other acute tissue injury without significant deleterious side effects. Additional potential uses include blockage of pain conduction in peripheral nerves, spinal cord, or brain and inhibition of smooth muscle relaxation in the gastrointestinal tract, lungs, and uterus.

DETAILED DESCRIPTION OF THE PREFERRED EMBODIMENT

Figure 1:
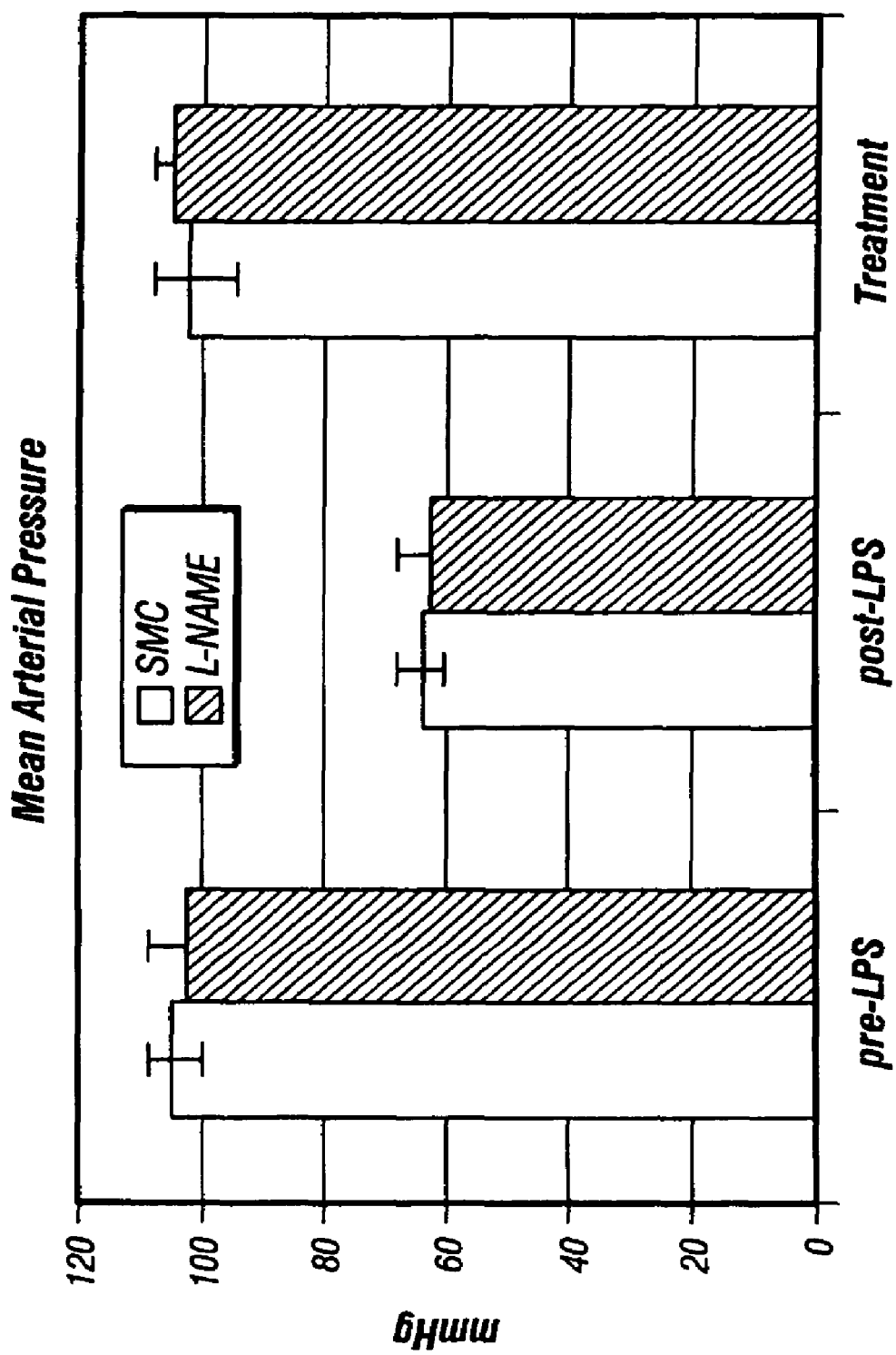
FIGS. 1 through 6 show the effects of treatments described in the examples in terms of comparison of an example of the invention antagonists to S-nitrosothiols, S-methyl-L-cysteine, to an inhibitor of nitric oxide synthase, L-NAME, in the treatment of an experimental model of septic shock.

Preferred compounds of the present invention can generally be described as S-alkylthiols. Most preferred are those that are S-alkylthiols of certain amino acids. Particularly preferred are S-ethyl-L-cysteine, S-methyl-L-cysteine, S-ethylglutathione, S-methylglutathione, S-methylcysteamine, S-ethylcysteamine, S-methylcoenzyme A and S-ethylcoenzyme A.

The treatment of patients may be with the compounds of the present invention or their salts. Such salts include salts with pharmacologically acceptable cations including, e.g., alkaline or alkaline-earth metals, specifically sodium, potassium or calcium, or salts with physiologically acceptable bases, e.g., simple amines such as ammonia. Also included are salts with pharmacologically acceptable anions including, e.g., chloride, bromide, iodide, sulfate, and phosphate. Esters and amides of S-alkylthiols may also be effective.

The compounds of the present invention may be formulated in a variety of ways. These include but are not limited to: solid forms, such as powders, granulates, tablets, capsules, liquid forms such as sterile injectable solutions, solutions or suspensions for oral administration; suppositories; aerosols; and topical or ingestible slow-release formulations. The formulations may include conventional additives, such as flavoring, excipients, stabilizers, effervescent agents, antioxidants, or the like. These additives will be used in conventional amounts and, with the exception of excipients, will usually be present in a total amount of less than about 10 wt. %. For slow release particles, various physiologically acceptable biologically degradable polymers may be employed, such as polylactates, polyglycolates, polyaldehydes, polyanhydrides, and the like.

Liposomes may also be employed as carriers, wherein the compounds of the present invention are present in the lumen of the liposome. Preparation of liposomes is conventional and is extensively described in the literature, and need not be described here. A further improvement in delivery of the therapeutic agent can be achieved, for those diseases where the disease is associated with specific cells, by conjugating to the liposomes molecules which provide for specific targeting. For example, antibodies may be bound to the liposome, either covalently or noncovalently, where the antibodies may be specific for oligodendrocytes, spinal ganglion neurons, chondrocytes or kidney cells.

Any convenient mode of administration of the compounds of the present invention may be employed. Administration may be oral, parenteral, via an enema, topical, or the like, such as by injection, oral tablet or powder solutions or other convenient means. Administration may be daily, multiple dosages per day, bidaily, by continuous administration, or any other convenient period.

The compounds of the present invention are administered in an amount sufficient to treat the disease. An amount adequate to accomplish this is defined as a "therapeutically effective amount" or "efficacious amount". Amounts effective for this use will depend upon the severity of the condition, the general state of the patient, the route of administration, and other factors known to those skilled in the art. For example, the doses of the compound could range from 1 mg to 10 grams daily, depending on the severity of disease and specificities of treatment.

One of the physiological actions of nitric oxide, largely through its conversion to peroxynitrite, is antimicrobial and nitric oxide is believed to play a major role in the defense against many types of bacterial, viral, and parasitic infections.

Nitric oxide is also a major component of endothelium-dependent vasodilation. In the original signal transduction pathway elucidated for endothelium-derived nitric oxide, nitric oxide is produced by isozymes of the enzyme nitric oxide synthase in endothelial cells (eNOS) in response to a variety of hormonal, mechanical, or other stimuli. Nitric oxide then diffuses out of the endothelial cells and into vascular smooth muscle cells where it activates the cyoplasmic enzyme soluble guanylate cyclase. The resultant increase in cytoplasmic cyclic GMP initiates a biochemical cascade that inhibits phosphorylation of myosin and consequently inhibits smooth muscle contraction.

In addition to the activation of soluble guanylate cyclase, nitric oxide also undergoes an oxidative reaction with thiols to form S-nitrosothiols (i.e. thionitrites). The nitrosation of cysteine side chains in various cytoplasmic and membrane-bound proteins has been associated with changes in enzyme activity, ion channel activity, or other types of signal transduction. It remains unclear whether such protein nitrosations in vivo occur by direct oxidative interactions between NO and the protein or whether NO is initially captured in low molecular weight nitrosothiols which then undergo double decomposition reactions with target protein thiols to form nitrosated proteins. We have previously demonstrated that neurons involved in the regulation of vasomotor tone contain pools of NO-derived factors that become depleted after repetitive stimulation in the presence of inhibitors of nitric oxide synthase. We have also demonstrated that neurons and endothelial cells contain intravessicular pools of NADPH diaphorase that has the chemical characteristics of a nitrosothiol (unpublished observations). In addition, intravenous injections of the specific nitrosothiol S-nitroso-L-cysteine produce a unique hemodynamic response profile when different vascular beds are compared, that is different from other nitrovasodilators including the D-isomer of S-nitrosocysteine. Nitric oxide itself is a relatively weaker vasorelaxant of small arteries than of large arteries, while S-nitrosocysteine is equally potent in small and large arteries.

While not wishing to be bound by theory, as opposed to result, the inventors believe that S-nitroso-L-cysteine, produced in endothelial cells and some neurons from NO and L-cysteine, and stored in cytoplasmic vesicles in those cells, acts as an endogenous endothelium-derived relaxing factor and neurotransmitter. The specific actions of S-nitroso-L-cysteine involve binding of S-nitrosocysteine to a stereoselective binding site on the target cell. If the overproduction of NO during septic shock also leads to increased production or release of S-nitrosocysteine then a specific inhibitor of S-nitrosocysteine binding might attenuate the hypotension of septic shock without affecting the potentially beneficial antimicrobial effects of nitric oxide and peroxynitrite.

We believe that a molecule structurally similar to S-nitroso-L-cysteine might be a competitor to S-nitroso-L-cysteine for the binding site. S-methyl-L-cysteine is such a compound, identical in structure to S-nitroso-L-cysteine except for the substitution of a methyl group in place of the nitroso group. In these examples, S-methyl-L-cysteine was found to inhibit the hypotensive effects of infused S-nitrosocysteine. In the present study S-methyl-L-cysteine not only attenuated the hypotension induced by lipopolysaccharide but did so without further impairing coronary blood flow, cardiac output, and heart rate. Total peripheral resistance returned to normal values with S-methyl-L-cysteine while treatment with L-NAME increased total peripheral resistance far above normal. The difference in the hemodynamic response between treatment with S-methyl-L-cysteine and treatment with L-NAME suggests that much of the hypotension in septic shock may be caused by overproduction of S-nitrosocysteine or some very similar compound. Inhibition of nitric oxide synthesis blocks NO-dependent vasodilation indiscriminately, leading to ischemia and organ failure even in the presence of normal mean arterial pressures. Inhibition of S-nitrosocysteine binding by S-methyl-L-cysteine selectively blocks the vasodilation caused by S-nitrosocysteine without affecting other NO-dependent vasodilations or other NO-dependent functions. Consequently, S-methyl-L-cysteine may be very useful in the treatment of septic shock.

The following examples offered to further illustrate, but not limit, the process and compositions of the present invention.

EXAMPLES

Male 16 week old Sprague-Dawley rats were anesthetized for surgical placement of intraaortic pressure tranducers and Dopplar flow probes around the abdominal aorta and the left main coronary artery. After 48 hours of recovery baseline measurements of arterial blood pressure, cardiac output (as Dopplar flow), and coronary blood flow (Dopplar) were obtained in conscious unrestrained animals. The rats were then treated with intraperotoneal injections of purified lipopolysaccharide 0.5 mg/kg. After 72 hours when the induction of iNOS had produced a fall in blood pressure, measurements were repeated. Each rat then received either 25 µmole/kg of the nitric oxide synthase inhibitor L-NAME or an infusion of 200 nmol/kg of S-methyl-L-cysteine for 10 minutes followed by a 500 nmol/kg bolus dose of S-methyl-L-cysteine. The measurements were then repeated a third time.

Figure 2:
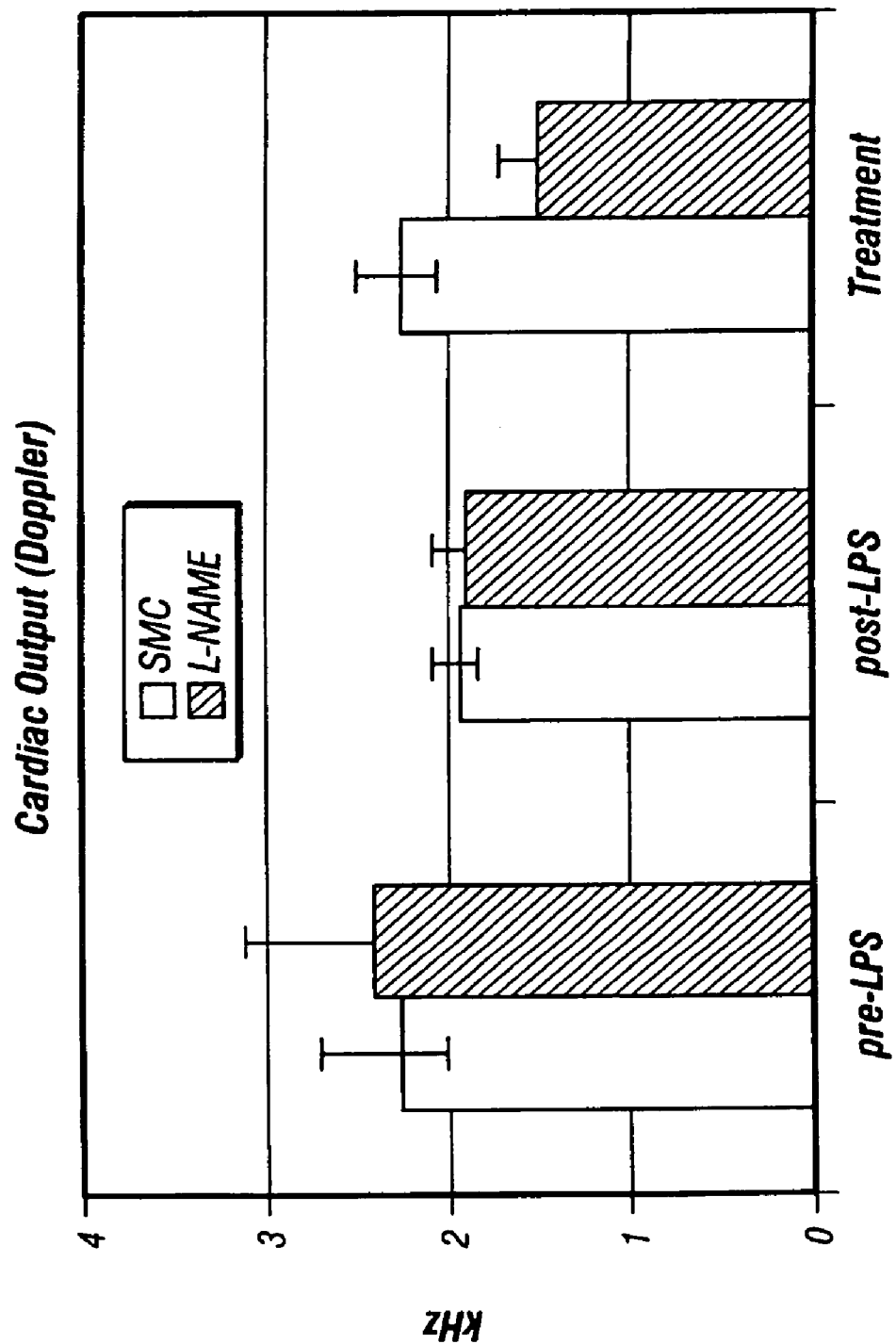
Figure 3:
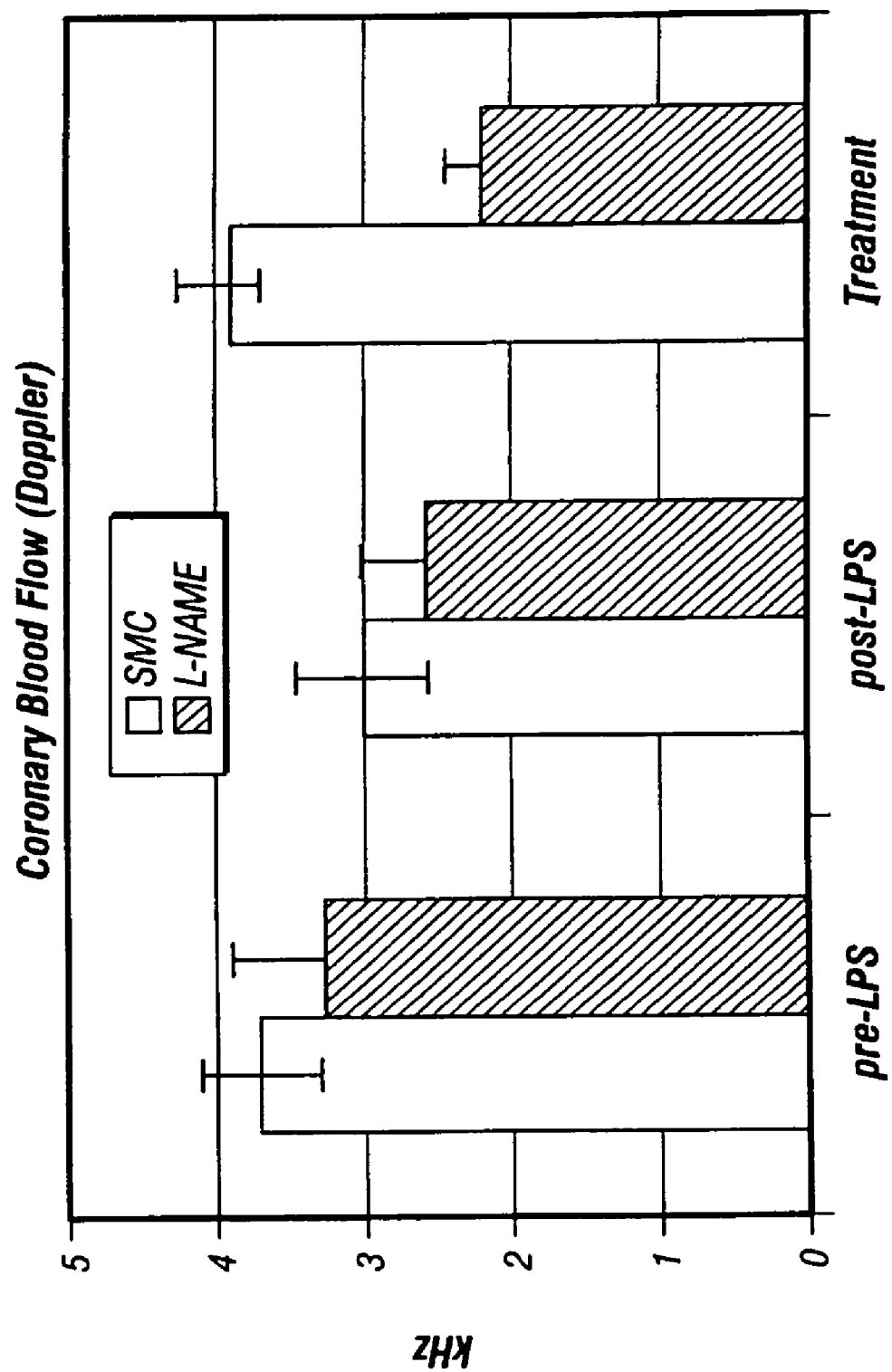
Figure 4:
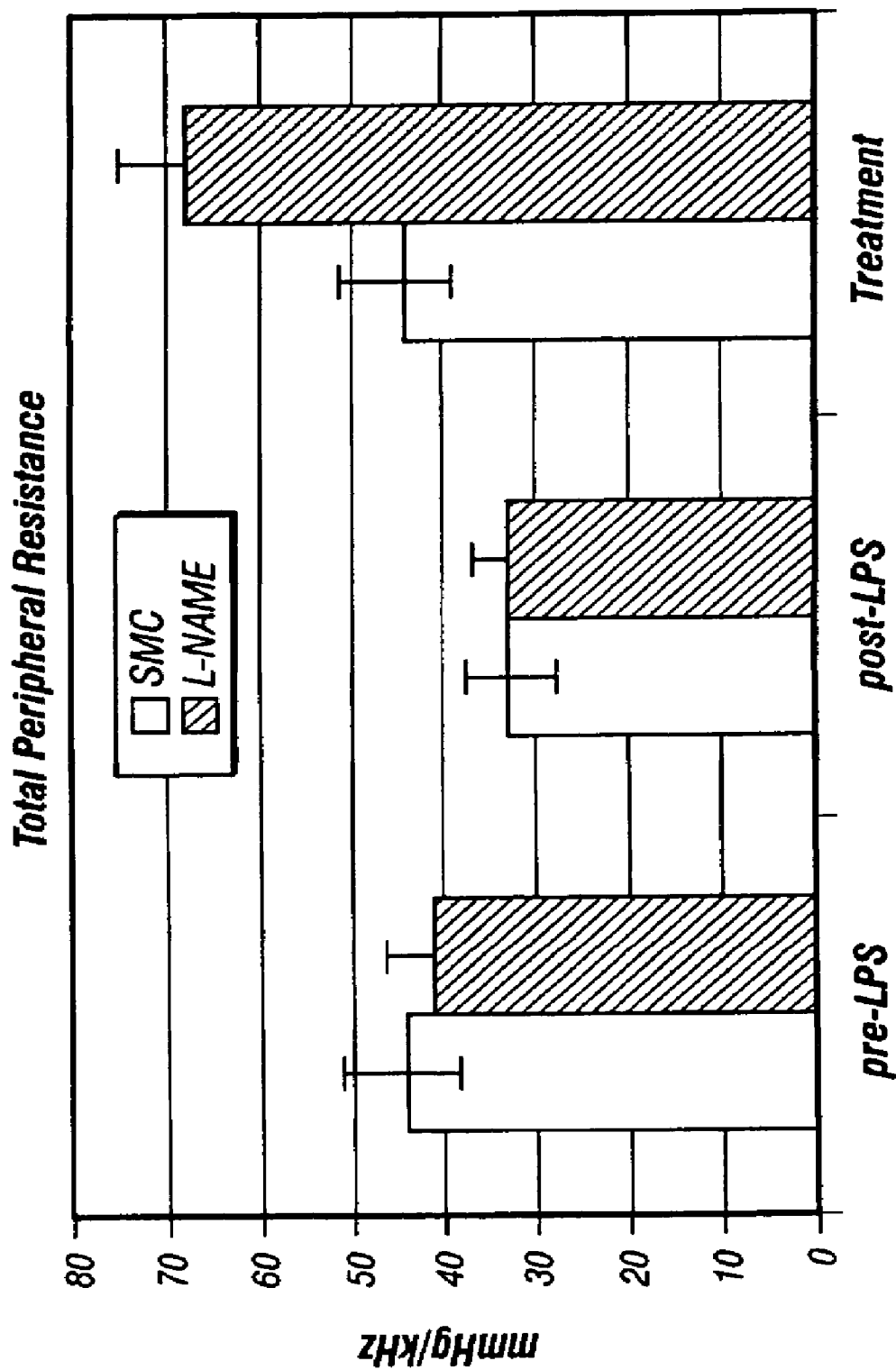
Figure 5:
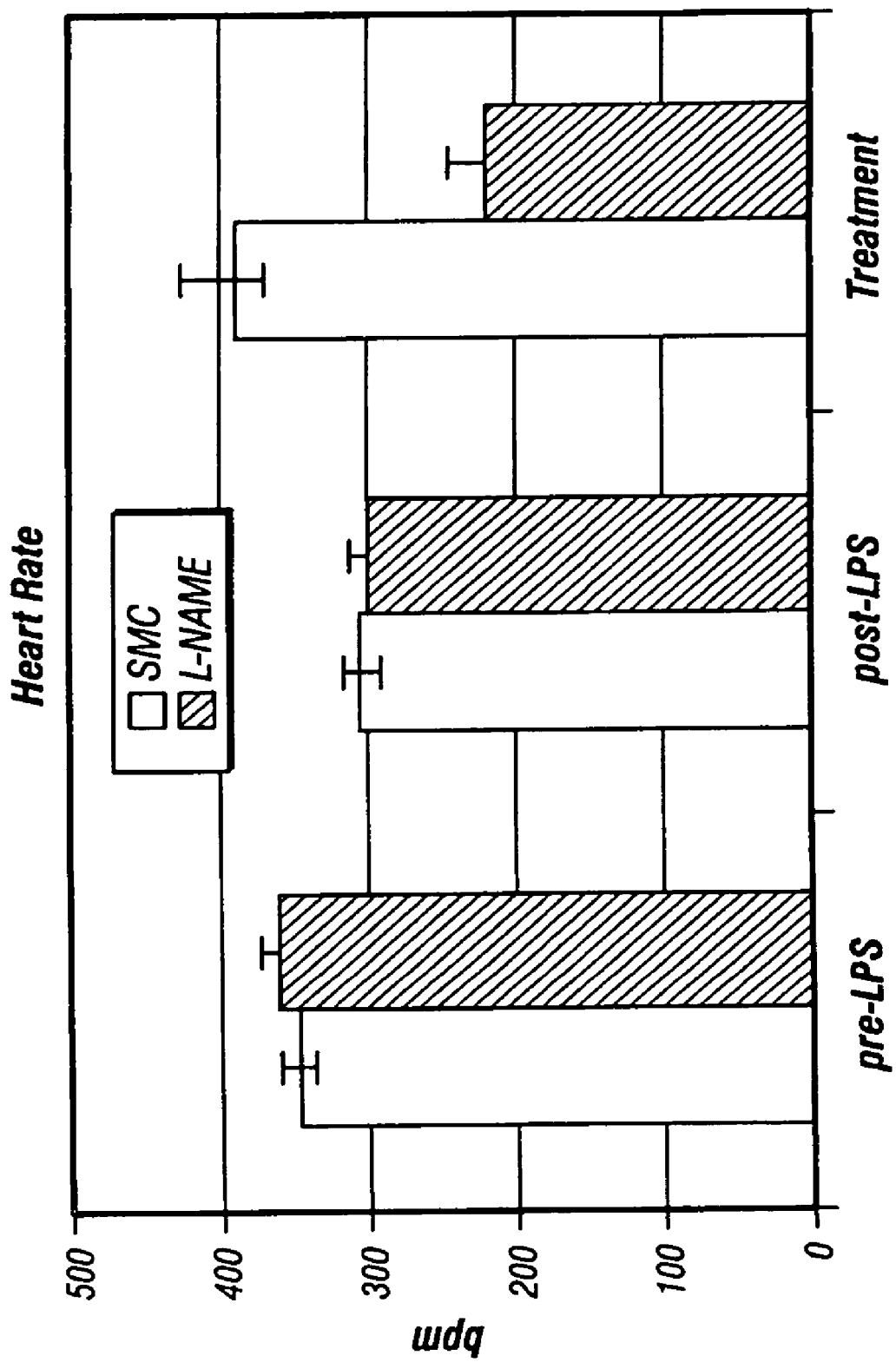
Figure 6:
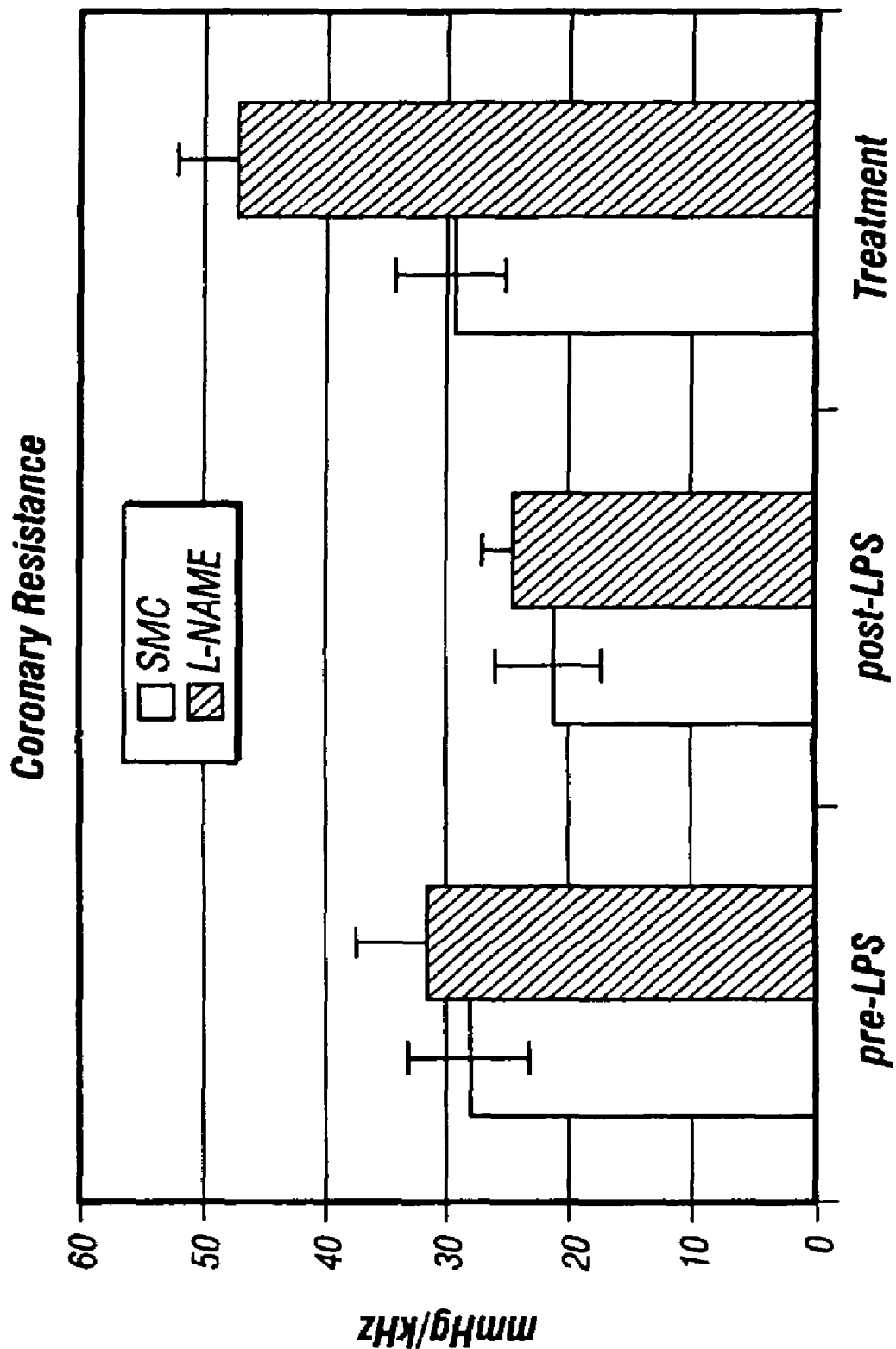

The results are summarized in FIGS. 1 to 6. After 72 hours of LPS exposure, blood pressure dropped 40%, heart rate dropped 15-20%, cardiac output dropped 20%, and total peripheral resistance dropped 25%. Both treatment with L-NAME and S-methyl cysteine returned mean arterial pressure to baseline values, but in the rats treated with L-NAME cardiac output, heart rate, and coronary blood flow dropped further to about 60% of the pre-treatment values while total peripheral resistance and coronary resistance increased to about 160% of baseline values. In contrast, treatment with S-methyl cysteine returned cardiac output, heart rate, total peripheral resistance, coronary blood flow, and coronary resistance to pre-treatment values. Twenty-two rats received L-NAME therapy and 7 died, while 12 rats were treated with S-methyl cysteine and none died. Twenty-eight rats received neither L-NAME nor S-methyl cysteine after treatment with lipopolysaccharide and one of those died.

What is claimed is:

1. A method of counter acting the overproduction of nitric oxide which often occurs in hypotension and shock, consisting essentially of:
   administering to a patient a therapeutically effective amount of an S-alkylthiol as an antagonist of S-nitrosothiols.

2. The method of claim 1 wherein the S-alkylthiol is selected from the group consisting of S-ethylcysteine, S-methylcysteine, S-methylcysteamine, S-ethylcysteamine, S-ethylglutathione, S-methylglutathione, S-methylcoenzyme A, and S-ethylcoenzyme A.

3. The method of claim 1 wherein the S-alkylthiol is selected from the group consisting of S-ethyl-L-cysteine, S-methyl-L-cysteine, S-ethylglutathione, S-methylglutathione, S-methylcysteamine, S-ethylcysteamine, S-methylcoenzyme A and S-ethylcoenzyme A.

4. The method of claim 1 wherein the S-alkylthiol is a pharmaceutically acceptable salt form.

5. The method of claim 2 wherein the S-alkylthiol is a pharmaceutically effective salt form.

6. The method of claim 3 wherein the S-alkylthiol is a pharmaceutically acceptable salt form.

7. The method of claim 1 wherein administration is intravenously.

8. The method of claim 1 wherein the dose ranges from about 100 mg to about 10 g.

* * * * *